United States Patent [19]

Fornoff

[11] 4,273,621
[45] Jun. 16, 1981

[54] PROCESS FOR DEHYDRATING ETHANOL AND FOR THE PRODUCTION OF GASOHOL THEREFROM

[75] Inventor: Louis L. Fornoff, Cedar Grove, N.J.

[73] Assignee: The Lummus Company, Bloomfield, N.J.

[21] Appl. No.: 146,550

[22] Filed: May 5, 1980

[51] Int. Cl.³ .................... B01D 3/00; B01D 53/04
[52] U.S. Cl. .................................. 203/19; 55/33;
    55/75; 55/76; 203/41; 568/916; 568/917
[58] Field of Search ............... 203/19, 41; 202/200;
    208/310 R, 310 Z; 568/913, 916, 917; 55/74,
    75, 76, 33, 35; 44/53, 54

[56] References Cited

U.S. PATENT DOCUMENTS

| | | | |
|---|---|---|---|
| 1,985,204 | 12/1934 | Derr et al. | 568/917 |
| 1,985,205 | 12/1934 | Derr et al. | 568/917 |
| 2,137,605 | 11/1938 | Derr | 203/41 |
| 3,122,486 | 2/1964 | Skarstrom | 203/18 |
| 3,132,079 | 5/1964 | Epperly et al. | 203/41 |

*Primary Examiner*—Frank Sever
*Attorney, Agent, or Firm*—James N. Blauvelt

[57] ABSTRACT

Process for dehydrating aqueous ethanol, utilizing a high-pressure distillation (with a single distillation column) of an aqueous ethanol admixture (preferably one derived from a conventional ethanol fermentation process), to achieve a vapor phase ethanol-water admixture containing about 90 percent, by weight, of ethanol, and then drying the vaporous admixture, in the presence of $CO_2$, with a crystalline zeolite type 3A, utilizing the "pressure energy" derived from the distillation to allow the product ethanol to condense at ambient temperatures, and then, if desired, employing the resultant dried ethanol product in the production of gasohol.

23 Claims, 5 Drawing Figures

PROCESS FOR DEHYDRATING ETHANOL AND FOR THE PRODUCTION OF GASOHOL THEREFROM

BACKGROUND OF THE INVENTION

1. Field of the Invention

The present invention relates to a process for dehydrating aqueous ethanol from a conventional aqueous ethanol source to a desired concentration by means of high-pressure distillation and drying of the product alcohol, and then, if desired, utilizing the product ethanol to produce gasohol. More particularly, the present invention relates to a process for dehydrating aqueous ethanol from a conventional aqueous ethanol source, such as the aqueous ethanol product derived from a conventional fermentation process, utilizing a single high-pressure distillation to achieve a vapor phase, ethanol-water admixture containing the desired ethanol concentration (e.g., about 78 mole % or 90 weight % ethanol), and then drying the resultant vaporous admixture with a 3A type crystalline zeolite in the presence of $CO_2$, utilizing the "pressure energy" derived from the distillation to allow the product ethanol to condense at ambient temperatures. If desired, the resultant dried ethanol product can be employed to make gasohol.

2. Description of the Prior Art

Dehydration of alcohols, particularly of ethanol, is a well-known art. Generally the methods used for dehydrating alcohols (and ethanol in particular) have either involved distillation of ternary azeotropes or non-distillation methods involving the use of various adsorbents. Many of the methods described in the patent literature have involved the addition of a third component to the binary water-ethanol azeotrope, which is soluble in water, but not ethanol, to product a ternary azeotrope, which is then subjected to distillation. The methods described in U.S. Pat. Nos. 2,140,694; 2,173,692; 2,358,193; 2,386,058; and 3,575,818; and in British Pat. No. 566,025; and in Polish Pat. No. 70,786—all fall within this category.

Additional specific examples for the dehydration of alcohols are set forth in a number of other representative patents. For example, U.S. Pat. Nos. 2,173,692; 2,358,193; and 3,575,818 describe the production of anhydrous ethanol by distilling a ternary azeotrope formed by adding diisopropyl ether, ethyl ether, pentane, and cyclohexane, respectively, to the binary azeotrope.

Non-distillation methods of dehydrating alcohols have centered upon the use of adsorbents, such as shown by U.S. Pat. No. 2,137,605; German Pat. No. 1,272,293; and Canadian Pat. No. 498,587, which collectively describe the use of either adsorbents or absorbents for drying ethanol including materials such as alumina, clinoptilolite, zeolite sodium-A, and bauxite, fuller's earth, and acid-activated bentonite.

While the foregoing patents are generally illustrative of the state of the art with respect to the dehydration of alcohols by either distillation or non-distillation means, it is also known in the art to combine these means under appropriate conditions. For example, U.S. Pat. No. 3,122,486 is concerned with an operation that combines a distillation operation with the use of a heatless fractionator for the purpose of treating aqueous azeotropic mixtures from a distillation unit, and this operation is said to be especially adaptable to production of high-purity anhydrous alcohols. The process of this invention consists of distillation of the crude alcohol to its azeotropic water mixture, followed by desiccation of the azeotrope by heatless drying over a water-selective adsorbent. Among the adsorbents taught by this patent are those that do not deteriorate when exposed to heat such as synthetic ion exchange resins. In general, such resins consist of polymers comprising a polystyrene that has been cross-linked with divinyl benzene and further treated, such as by sulfonation.

Also of some interest with respect to this combination of means is U.S. Pat. No. 3,132,079, which is directed to the removal of water from water-isopropanol mixtures to yield a pure isopropanol stream. In this patent, a distillation column is utilized to effect a substantial amount of separation of a crude alcohol feed; but, since the purity of the alcohol-rich product is limited by the alcohol-water azeotrope, the azeotropic mixture has to be removed as an overhead product and thereafter treated with an adsorbent. A variety of crystalline aluminosilicates (molecular sieves) are expressly mentioned as being equally useful for this purpose, including a large number of molecular sieves having pore openings in the range of about 3–10 Angstrom units. Alternatively, silica gel or alumina is also said to be utilizable as an adsorbent in such a system.

However, the latter two U.S. patents, although broadly suggestive of some aspects of the present process, nevertheless, are deficient with respect to the objectives, results, and means for obtaining same expressed in the present invention.

U.S. Pat. No. 3,122,486, for example, is not cognizant of the fact that: (1) high-pressure distillation should be used, and, if used, can be used to unexpected advantage as, e.g., in permitting the condensation of product ethanol to be obtained at ambient temperatures; and that (2) adsorption of the overhead from such high-pressure distillation can be conducted in the vapor phase, in the presence of $CO_2$, thereby avoiding the disadvantages of co-adsorption such as is experienced in U.S. Pat. No. 3,122,486 and concurrently gaining the unexpected advantages mentioned above.

This patent, moreover, is dependent upon "pressure swing" in order to be operative, and also requires the use of a vacuum pump in order to obtain the pressure ratio required between adsorption and desorption. The present process is not subject to such deficiencies and limitations.

U.S. Pat. No. 3,132,079, in general, deals with thermal regeneration of the adsorbent it uses, and, in order to be operative, requires the use of a heater for its regeneneration process. In addition, this patent is unable to avoid the problem caused by co-adsorption of ethanol by its adsorbents, and also fails to appreciate the concept of water selectivity.

Not disclosed or suggested by the above patents, and unknown to the art, in general, however, are a number of important features which are characteristic of the present invention (and will be described in detail later) and which are also important to its successful practice; these features include, for example, (a) the use of carbon dioxide, preferably derived from the crude ethanol feed source and contained therein (e.g., in the form of a by-product), or $N_2$, as a means with which to effect a number of concurrent functions such as the storage of the heat of adsorption, a means for temperature control and a desorption purge material with which to desorb the water impurity; (b) the use of a type 3A molecular sieve adsorbent (or natural crystalline zeolites having a pore size of 3 Angstroms) exclusively, since all other commercially available crystalline zeolites or molecular sieves, as well as carbon, alumina, and silica gel would co-adsorb ethanol and $CO_2$; (c) the use of high pressure (i.e., 50 p.s.i.a. or more) distillation so as to permit condensation of the dried product ethanol at ordinary temperatures of, e.g., 80° F.–100° F.; (d) the absence of a need to utilize conventional swing adsorption, since a relatively low pressure ratio between the adsorption and desorption steps or stages can be utilized through the use of a circulating stream of $CO_2$, etc.

The interaction of these and other features enables the present process of dehydrating ethanol to operate without need of any thermal energy beyond the energy used to the first stage distillation column, and only about 0.5% of the ethanol potential, in the form of electrical power, that is needed to totally dehydrate the ethanol from 90% to 100% by weight ethanol. The energy cost savings of this are so enormous as to render economically feasible and attractive the production of gasohol from the dried ethanol product produced in accordance with the practice of the process of this invention as an alternative to the production of gasoline.

SUMMARY OF THE INVENTION

The present invention provides a more efficient and less expensive process for dehydrating ethanol than has been known heretofore in that it provides a high-pressure process for distilling, in a single distillation, a crude aqueous ethanol feed at pressures of at least about 50 p.s.i.a., to achieve a vapor phase ethanol-water admixture comprising at least about 75 mole %, preferably 78 mole % (90 weight %) ethanol whose water content can later be adsorbed from the admixture. Pressures of less than 50 p.s.i.a. are insufficient for purposes of this invention since they do not allow convenient condensing of the dry ethanol product that results from adsorption. The overhead product from this high-pressure distillation constitutes a vaporous ethanol-water admixture comprising, as noted, about 90 weight % ethanol and the balance essentially water. It is required that this admixture be, and be kept in, the vapor phase in order to accommodate the ease and success of the adsorption (and desorption) phase of the present process.

In order to concentrate the ethanol content of the overhead vaporous ethanol-water distillation product still further, it is necessary that its water content be adsorbed therefrom, and this can only be done, in accordance with this invention, with a type 3A synthetic crystalline zeolite or a naturally occurring crystalline zeolite which, by virtue of its pore size of 3 Angstrom units, excludes passage therethrough of ethanol and $CO_2$ molecules but adsorbs those of water thereby enabling the production of a "bone dry" concentrated ethanol product.

The adsorption phase is effected by diluting the distillation overhead vapor with a circulating stream of $CO_2$, preferably one derived from a conventional ethanol source such as one resulting from a conventional ethanol fermentation process; and then passing the thus-diluted vaporous product through an adsorption zone comprising a 3A crystalline zeolite to adsorb water from such vaporous product, utilizing the "pressure energy" derived from the distillation to allow the product ethanol to condense at ambient temperatures, e.g., 80° F., and allowing the remaining $CO_2$ to be used to regenerate the zeolite adsorbent.

BRIEF DESCRIPTION OF THE DRAWINGS

The above and other features and advantages of the present invention will become more readily apparent from the following description with reference to FIGS. 1-4 of the attached drawings.

DESCRIPTION OF THE PREFERRED EMBODIMENT

Figure 1:
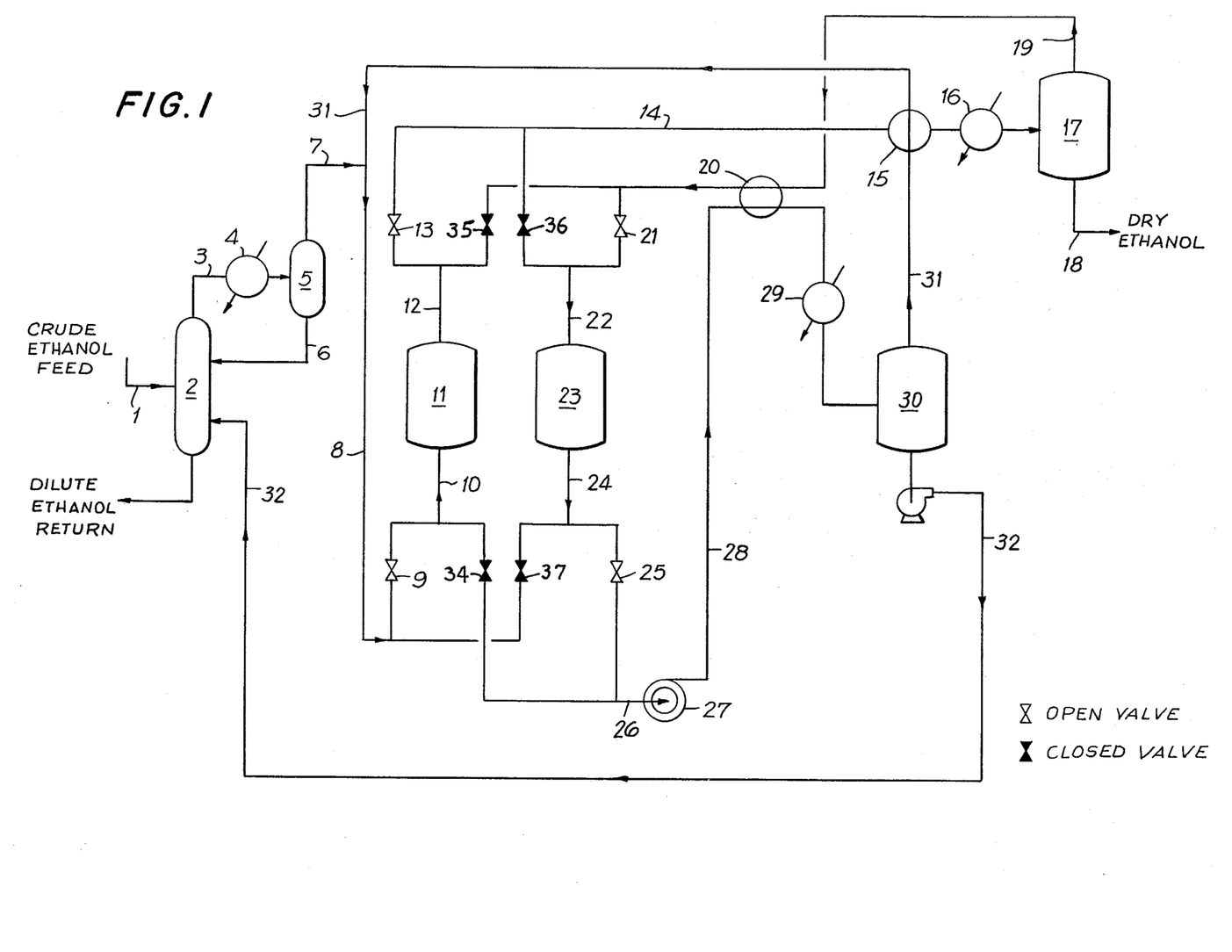
FIG. 1 illustrates a broad embodiment of the present dehydration process wherein a series of 2 adsorbent vessels is used.

With reference to FIG. 1, a crude aqueous ethanol feed 1, such as one derived from a conventional alcohol fermentation process and containing about 4%–12% by volume dilute ethanol, preferably filtered, is pressurized by a pump (not shown) to an elevated pressure in excess of about 50 p.s.i.a., e.g., such as 110 p.s.i.a. and fed to a distillation column 2 which is operated in a manner such as to generate a gaseous overhead stream containing at least about 75 mole % ethanol. This overhead product is passed, via transfer line 3, through heat exchanger 4—which functions as a partial condenser, condensing sufficient liquid to satisfy the reflux requirements of the distillation column 2—into vessel 5, which acts as a separator returning the reflux to distillation column 2, via line 6, and transmitting a gaseous ethanol overhead stream, via line 7, that is introduced into a stream (line 31) of circulating $CO_2$ that has been preheated in heat exchanger 15 to at least 140° F. so as to enable the resultant $CO_2$-enriched, gaseous ethanol-$H_2O$ mixture to remain above 170° F. (the dewpoint of ethanol in said mixture). The hot circulating $CO_2$ also dilutes the $H_2O$ concentration present in the ethanol mixture from a level of about 20–25 weight % to a level of about 5 weight %. The temperature and composition of the combined stream preferably are adjusted so as to ensure that such stream is unsaturated with respect to its water and ethanol content. In the preferred embodiment of this invention, the combined stream is at a temperature between about 180° F. and about 200° F. and contains about 5 weight % water and about 16 weight % ethanol.

Figure 4:
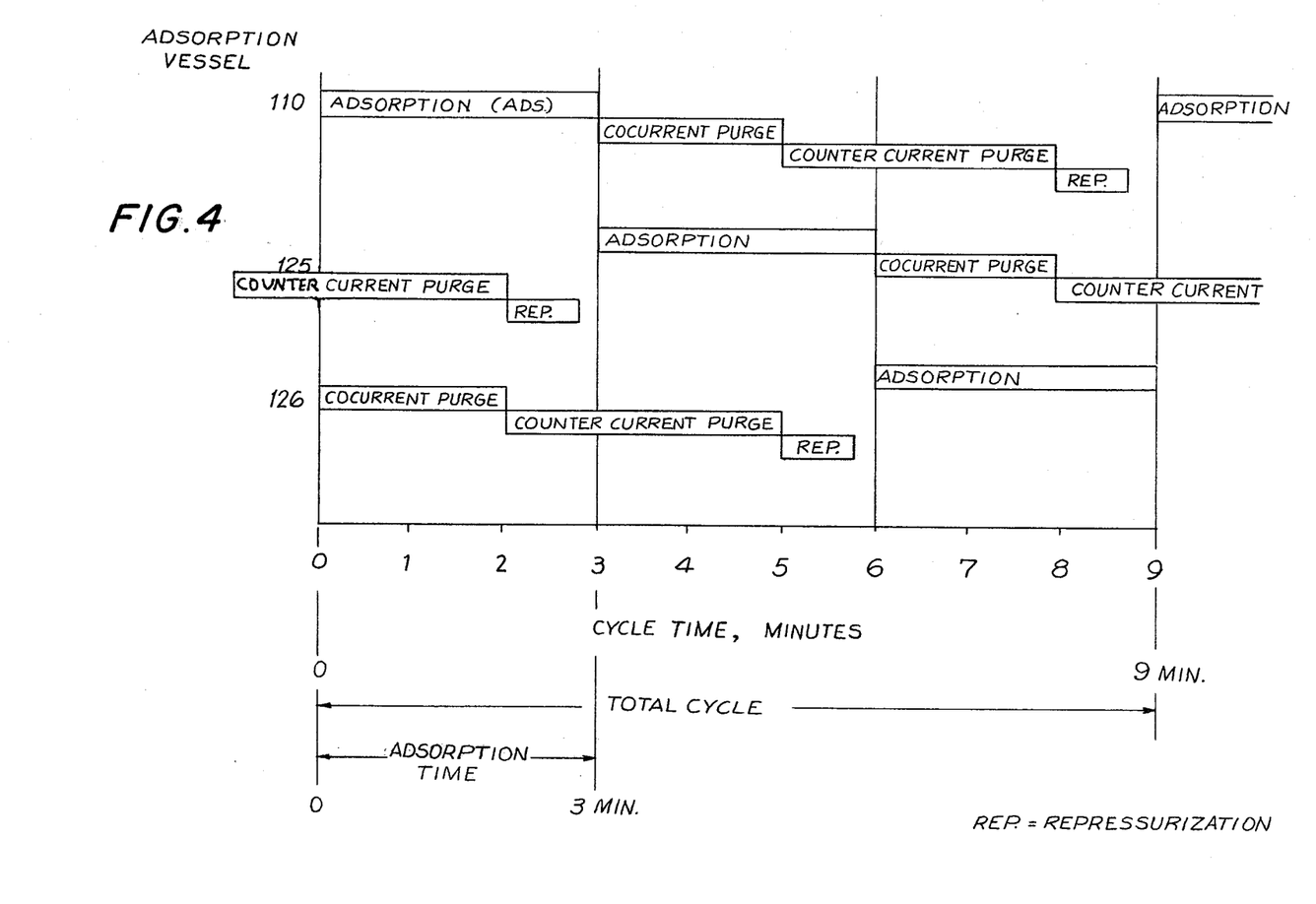
FIG. 4 illustrates a bar chart showing the preferred sequence of process steps for the three adsorption vessels 11, 126, and 127.

The combined stream is then passed, via line 8, through valve 9, and, via line 10, through a series (11 and 23) of at least two adsorbers containing natural or synthetic crystalline aluminosilicate 3A such as type 3A molecular sieves manufactured by Union Carbide, whereby $H_2O$ alone from the $CO_2$, $H_2O$ and ethanol mixture is selectively adsorbed. For the purposes of this invention, a minimum of two adsorbers is needed to accommodate the adsorption of $H_2O$; however, it is preferred that the adsorption process be effected continuously in the form of cycles so as to accommodate systematic adsorption and desorption of the $H_2O$ to be removed and a purge of the residual vapors. Thus, it is preferred that a series of three adsorber vessels be used, most preferably in a sequential fashion that takes into account efficient staging of the adsorption, desorption, and purging phases, an exemplary form of which is illustrated in FIG. 4.

Figure 3A:
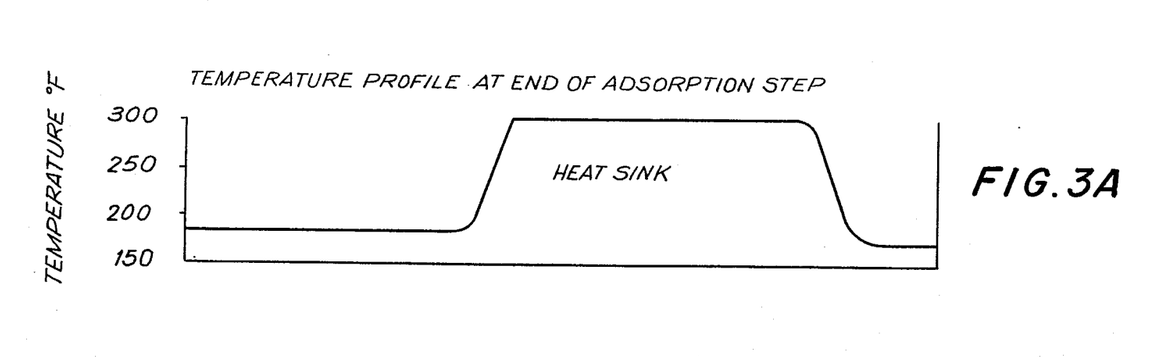
FIGS. 3A-B illustrates a temperature profile at the end of the adsorption and stripping steps.
Figure 3B:
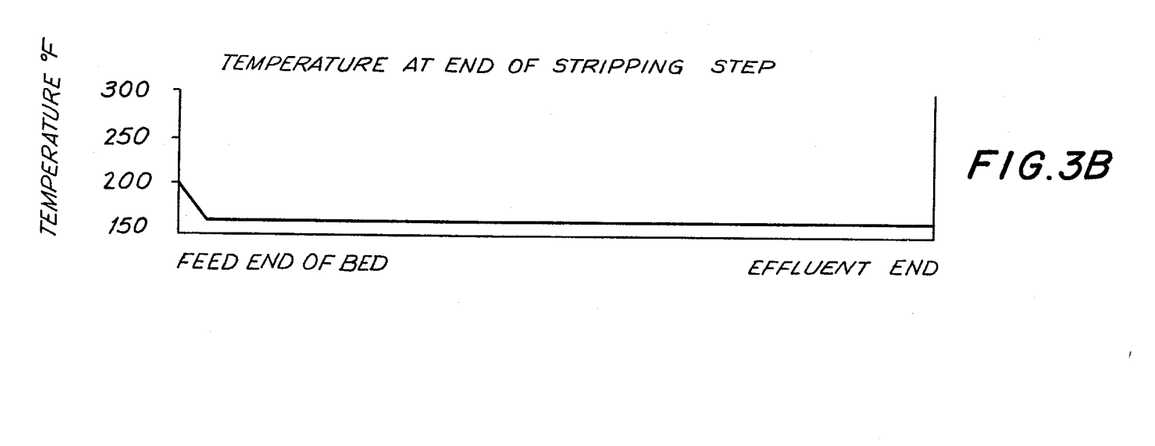

The adsorption process generates a heat of adsorption which causes a temperature rise of about 110° F., and this sensible heat thus generated can serve as a means of heating up the zeolite adsorbent (downstream of the adsorption zone) which becomes the source of heat for subsequent regeneration of the adsorbent. The temperature profile of this process is shown in FIG. 3A. The $CO_2$-ethanol-$H_2O$ overhead coming in behind the adsorption front cools the front end of the adsorbent bed and adsorption continues.

At the pressure and temperature levels which prevail at the start of adsorption, significant adsorption of $H_2O$ takes place rapidly, e.g., to a extent, on the average, of up to about 16-20% by weight, of the weight of the zeolite 3A adsorbent. Thereafter, the adsorption rate declines rapidly so that, after passage of the gases through only 20-40% of the adsorbent, the adsorption level already has dropped to about 4-8% (weight of water adsorbed/total weight of adsorbent). Thus the heat of adsorption, which tends to roughly vary with the rate of $H_2O$ adsorption by the zeolite, is displaced forward from the adsorption zone in view of frictional and other factors associated with the fluid flow through the adsorbent. This results in the sensible heat of adsorption being substantially confined to intermediate depths in the adsorbent bed approximating between 40%-85% of its total depth. As would be obvious to those skilled in the art, therefore, consistent with the foregoing, the adsorbent particle size and amount, adsorber vessel length/diameter ratio and Reynolds number are controlled in such fashion as to generate a sufficient heat transfer coefficient to sweep the heat generated forward and keep it in the adsorbent vessel as well as the water adsorbed. The physical form and arrangement, and deployment, of the adsorbents and the adsorption cycle time are susceptible to a considerable variety of choices and possibilities to take advantage of this feature. Thus the artisan can alter the depth and size and shape of the adsorbent bed and number and arrangement of beds, consistent with his desires as to adsorption, as well as the particle size and shape of adsorbent, and the dimensions, configurations, and materials of construction of the adsorbent container.

The dried vapors that exit from adsorbent vessel 11 are passed, via line 12, valve 13, and line 14, through heat exchanger 15 which cools them and heats the circulating $CO_2$ vapor in line 31. The cooled, dried vapors are then further cooled in heat exchanger 16 to a temperature of about 80° F., whereupon about 90% of the ethanol is condensed, and the resultant cooled mixture is then fed to a separator vessel 17, which separates anhydrous ethanol from the circulating $CO_2$. The anhydrous ethanol product passes from separator vessel 17, via line 18, and is recovered. It can, if desired, be utilized as a feedstock for gasohol.

The overhead vapor from separator vessel 17, which contains about 2% ethanol, 98% $CO_2$, and only a trace of $H_2O$, is passed, via line 19, through heat exchanger 20, where it is heated to about 150° F.-200° F., and then passed, via valve 21 and line 22, into a second adsorption vessel 23. The hot, dry vapor strips the adsorbed water from the 3A molecular sieve adsorbent contained in adsorption vessel 23, thereby regenerating the adsorbent for adsorption of a fresh dilute $CO_2$-$H_2O$-ethanol admixture derived from distillation column 2.

The wet vaporous bottoms product from adsorption vessel 23 exits, via line 24, through valve 25 and line 26. The bottoms product contains the water adsorbed in adsorption vessel 23 during the adsorption cycle.

The wet vapor (from adsorption vessel 26) is then fed, via line 26, to compressor 27, where it is recompressed to an extent sufficient to compensate for the pressure drop that has previously been experienced in the system. If desired, an additional pressure drop can be engendered in line 19 so as to generate additional gas volume for stripping water adsorbed in adsorption vessel 23.

Figure 2:
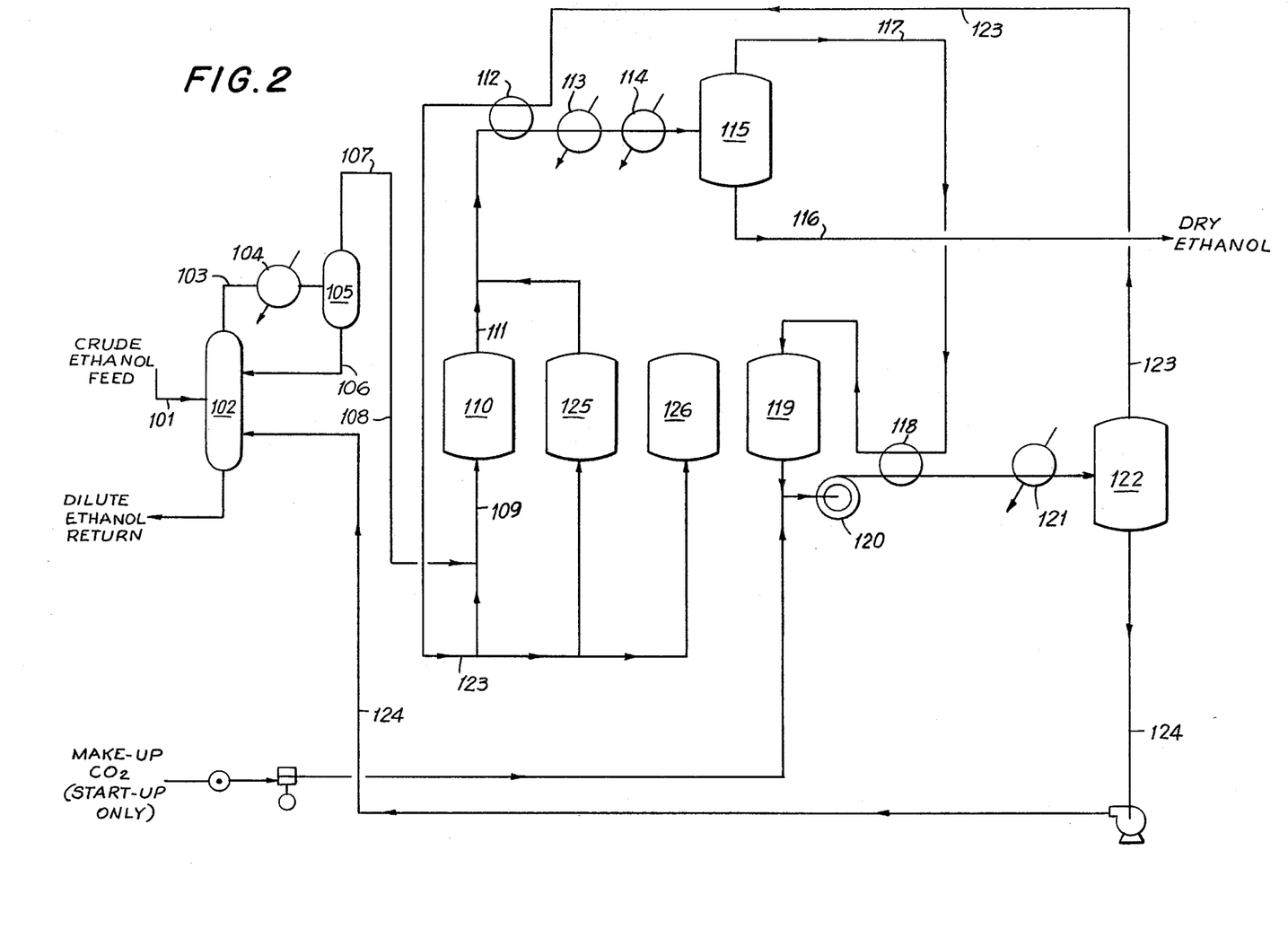
FIG. 2 illustrates the preferred embodiment of such process wherein a series of 3 adsorbent vessels is used.

While the desorption phase of the present dehydration process has been discussed with particular reference to the adsorption vessel 23, it is apparent from FIGS. 1 and 2 that the desorption phase would be operable in the same manner for other adsorption vessels, e.g., such as adsorption vessel 11, 110, 126, and 127, depending upon the particular stage of the dehydration process cycle being operated.

The compressed vapor from compressor 27 is passed, via line 28, through a heat exchanger 20, where it is partially cooled and then further cooled in heat exchanger 29 to a temperature of about 95° F. during which time about 50% of its ethanol content and about 85% of its water content are condensed. The cooled vapor and condensate then enter vessel 30, which separates the mixture into a water-saturated $CO_2$ mixture and an ethanolic solution containing about 29% ethanol by weight.

The overhead vapor from vessel 30, rich in $CO_2$, is then allowed to circulate in the system, via line 31, and dilute the ethanol-water overhead stream 7 from vessel 5, which, as a combined stream 8, is fed to adsorption vessel 11.

The 29 weight % ethanol bottoms from vessel 30 is pumped back to distillation tower 2, via line 32, preferably to a tray thereof that also contains 29 weight % ethanol.

When (and while) adsorption vessel 11 is being regenerated, adsorption vessel 23 can be placed in the adsorption cycle by closing valves 9, 13, 21, and 25 and by opening valves 33, 34, 35, and 36.

As previously explained, the present dehydration process and system can be conducted with two adsorption vessels operating in series. However, with such a scheme, the ethanol contained in the void volume of the vessels has to be combined with the regeneration water and the resulting combined entities recycled, thereby resulting in a loss of efficiency which can be avoided or eliminated by adding one or more adsorption vessels. For example, addition of a third adsorption vessel to the system shown, as a broad embodiment, in FIG. 1 would enable a cocurrent purge to be made, with circulating $CO_2$ gas, of an adsorption vessel that had completed its adsorption cycle. Such a feature would enable ethanol to be swept from the void volume of the vessel concurrently while adsorption was being effected in another adsorption vessel.

In FIG. 2, as mentioned above, the preferred embodiment (i.e., the best mode) of the present invention is set forth. The process scheme set forth in FIG. 2 differs from that of FIG. 1 essentially in that four adsorption steps (i.e., adsorption, cocurrent purge, desorption, and repressurization) instead of two are employed. If desired, two of these steps: cocurrent purge and repressurization can be carried out in one vessel and effected while adsorption and desorption, respectively, are being concurrently effected in the other two adsorption vessels. Thus the process steps prior to adsorption, as can be seen, are the same for both FIGS. 1 and 2 and as described above.

With reference to FIG. 2, utilizing reference numerals in the "100" series, it can be seen that the description of the present process equipment members 1-8 and 101-108 and their mode of operation is identical for the process steps prior to adsorption; thereafter, operation of the preferred embodiment of this invention may be seen from the following description, read in conjunction with FIG. 2.

Passed into a 3A molecular sieve-containing adsorber 110, via line 109, is a combined stream containing a $CO_2$-enriched-ethanol (about 78 mole % ethanol) and $H_2O$ gaseous admixture at a temperature of at least 170° F., whereby $H_2O$ alone is selectively adsorbed from the admixture. The dried gas from adsorber 110 exits, via line 111, and passes through heat exchangers 112 and 113 (and optionally—as explained below—heat exchanger 114, when circumstances warrant its use) which cools it to a temperature sufficient to condense most of the ethanol and also heats the circulating $CO_2$ vapor in line 123. Heat exchanger 114 is an optional refrigerated water cooler which can be used during warm weather when the cooling water temperature used in the heat exchanger 113 exceeds 70° F. The cooled mixture then enters separator 115 which separates anhydrous ethanol from the circulating ethanol. The anhydrous ethanol product passes from separator 115, via line 116, and is recovered.

Separator 115 removes about 95.5% of the ethanol as anhydrous ethanol product. The overhead from separator 115, which comprises a dry mixture of 1.7% ethanol and 98.3% $CO_2$, is passed, via line 117, to heat exchanger 118 and heated to 150°-200° F.

The dry gas is passed countercurrently through regeneration vessel 119 where it strips the water from the adsorbent bed of type 3A molecular sieve. It also pushes the heat front back from the storage zone of the bed, i.e., the part where the heat of adsorption is "stored" and the concentration of water is least. In the desorption zone, the temperature is about 145° F.; and the gas leaving the desorption zone, which is about 70-100% saturated with $H_2O$, is passed into compressor 120 wherein it is compressed from about 81 to 94 p.s.i.a. and then passed through heat exchangers 118 and 121 to separator 122. From separator 122, a bottoms product, comprising an ethanol stream containing about 29% by weight ethanol is removed, via line 124, and pumped back to distillation column 102, which maintains the water balance at the overall fermentation/distillation-/adsorption complex.

The overhead product 123 from separator 122 then is divided into two streams: a dilution stream, which provides the major portion of the circulating $CO_2$ stream used to dilute the overhead product of distillation column 102; and a purge/repressurize stream which can be used to purge adsorption vessel 125 and repressurize adsorption vessel 126 or vice versa.

In the preferred embodiment of this invention, the purge/repressurize steps represent different parts of the same cycle step as shown in FIG. 4. Over this three-minute step, 30 seconds is used to repressurize after the purge step. For the remaining 2½ minutes, the gas is used to purge the ethanol out of the void volume of the adsorber following the adsorption step, i.e., about two void volumes of purge gas are used to sweep out the adsorber. The preferred sequence of events for each of the three adsorbers is as follows: 0-180 seconds—adsorption; 180-330 seconds—co-current purge; 330-510 seconds—regeneration; and 510-540 seconds—repressurization.

As shown in FIGS. 1 and 2, $CO_2$ is recycled continuously and, theoretically, once the prescribed amount of $CO_2$ is introduced into the present process at the start thereof, no further $CO_2$ is required. However, for start-up purposes, and in the event of leakage, a small $CO_2$ compressor can be employed to take $CO_2$ from the fermentation cells and compress it to 85 p.s.i.a. for whatever use may be required of the compressed $CO_2$.

As has been seen, the present dehydration process is one acutely conscious of energy costs, and, in this connection, especially suitable for operation without need of any thermal energy beyond that which is used in distilling the crude alcoholic (e.g., ethanolic) feed to achieve an overhead gaseous product, of desired alcoholic concentration, e.g., one containing about 90 weight % ethanol (which is considerably less than the energy needed to distill alcohol to its 95 weight % ethanol azeotropic concentration). Thereafter, the energy saving embodied by such product is preserved and utilized subsequently to help allow the ultimate alcoholic product to condense at ambient temperatures. However, to achieve this result, in accordance with the best mode of practice of this invention, it is commercially necessary that pressures of at least 50 p.s.i.a. and preferably higher be utilized during distillation of the crude alcohol. This pressure limitation, however, is a matter of practical, rather than theoretical, concern, since, theoretically, lower pressures could be employed. Nevertheless, under current process conditions and cost levels, it is not economically feasible to conduct the present distillation at pressures lower than 50 p.s.i.a., since, e.g., more costly cooling measures would have to be adopted.

One of the most attractive features of the present process is that is combines the best features of distillation and non-distillation means to maximum advantage without incurring the disadvantages associated with either of them. This has largely been accomplished through the use of vapor phase adsorption and a circulating $CO_2$ gaseous stream, which is derived in the form of a by-product when the crude alcohol feedstock to be employed is derived from fermentation processes. Heretofore, co-adsorption of alcohol and poor water selectivity have characterized the performance of prior art adsorbents that have been used to dehydrate alcohols. However, in the present invention, by conducting the adsorption in the vapor phse, and doing so with an adsorbent uniquely suited for this purpose, i.e., a type 3A molecular sieve adsorbent for a natural crystalline zeolite having a pore size of about 3 Angstroms eliminates the co-adsorption problems and enables the $H_2O$ contaminant to be selectively removed on a highly efficient basis. At the same time, the combination of these features can be further enhanced by controlled use of the heat of adsorption generated during the $H_2O$ adsorption process. In this invention, positive steps are taken to confine the sensible heat of adsorption to intermediate adsorbent levels contained in the adsorption vessel used and to keep such sensible heat within the vessel so that entering and exiting process material flows can heat up or cool the adsorbent and thereby aid in its functioning. The circulating $CO_2$ stream not only is of use in this regard but has the additional multiple advantages of controlling temperature (in the adsorbers and elsewhere) and of being of use in desorbing or purging residual vapors such as $H_2O$.

The present dehydration process is especially suited for automation in view of the fact that its individual steps or stages can be integrated into sequences that can be carefully monitored and precisely controlled, as, e.g., by timers or computers. As previously seen, there is considerable latitude afforded the process operator in terms of the adsorption, desorption, purge, and repressurization phases of the present process. For example, a series of at least two adsorption vessels is required in order to have concurrent adsorption and desorption. However, a third adsorption vessel is needed in order to gain the advantage of having adsorption, desorption, and purging all being done concurrently and the benefits of fully continuous operation. If desired, even a fourth adsorption vessel could be used, but, with its addition, would come a period of idleness in the system, along with added cost, which could only be justified in the event operating problems associated with one or more of the other three adsorption vessels caused them to be inactivated or otherwise inoperable.

While the ideal or most preferred alcoholic feedstock of the present invention is one derived from conventional fermentation processes (because $CO_2$ is included in the feedstock), other alcoholic feedstocks can be utilized along with an independent source of $CO_2$ or any other inert gas operable under the present process conditions such as nitrogen, such as one to which the process operator has access, as, e.g., from another part of his plant complex.

Conventional fermentation processes include natural fermentation processes wherein almost any agricultural raw material with a carbohydrate content in the form of sugars or starches that are easily converted to sugars can be used. Once the raw materials are in the form of sugars, yeast enzymes are added to commence natural fermentation. Heretofore, industrial alcohol has been traditionally prepared by fermentation of blackstrap molasses, which contains up to 50% sugars and can be easily fermented. The starting mash is prepared by diluting the molasses with $H_2O$ to bring the sugar content down to about 15 weight %, after which enzymes such as invertase (to convert sucrose) and zymase (to convert glucose and fructose) are added. The fermentation ethanol end product consists essentially of ethyl alcohol and $CO_2$. Yeast activity is sustained by the addition of nutrients. With careful control of temperature and acidity, the fermentation process is ordinarily completed in about two days and the resulting mash, usually containing about 12% ethyl alcohol, is recovered by distillation. The crude fermentation product is preferably filtered before being fed to the distillation column.

As previously mentioned, the ultimate ethanol product produced by the present dehydration process is suitable for the manufacture of gasohol. The use of alcohols to fuel gasoline engines while old in the art (as shown in a Farmer's Bulletin issued by the U.S. Department of Agriculture in 1907) has heretofore been discouraged by the unfavorable economics and availability of the alcohols suggested for such use, viz., methanol and ethanol. However, ecological and environmental preferences for fuel obtained from renewable rather than fossil sources, along with political factors promoting the use of domestic sources of fuel such as surplus farm products, have produced a strong driving force in the direction of blends of alcohol with gasoline, particularly blends of ethanol and gasoline. Since blending of fermentation ethanol with gasoline is now being promoted by sizeable state and federal subsidies, there is considerable incentive in reducing the production costs of a dehydrated fermentation ethanol suitable for Gasohol use. The present invention now provided an excellent basis for filling this void, and making the manufacture of Gasohol from ethanol competitive.

The present invention provides an economical process for the production of gasohol, in varied ethanol-gasoline blends, comprising dehydrating aqueous ethanol, as previously described, through high-pressure distillation of a crude fermentation ethanol feed to obtain an overhead mixture containing at least about 75 mole %, preferably 78 mole % ethanol; drying of such overhead with a type 3A crystalline zeolite in the presence of an inert gas of $N_2$ or $CO_2$, preferably $CO_2$; condensing the dried ethanol at ambient temperatures; recovering the anhydrous ethanol; and mixing the anhydrous ethanol with gasoline in suitable proportions such as up to about 10 weight % anhydrous ethanol to 90 weight % or more gasoline.

The type 3A molecular sieves that may be employed in the practice of this invention include both naturally occurring and synthetic zeolites having a pore size of about 3 Angstroms (e.g., at least 2.6 Angstrom units, but less than about 3.6 Angstrom units), thus allowing only water to be adsorbed. A description of such zeolites may be found in *Zeolite Molecular Sieves* by Donald W. Breck, published by John Wiley & Sons, Inc., New York 1974, whose disclosure in this regard is hereby incorporated herein by reference. Most useful is the synthetic 3A (i.e., potassium exchanged zeolite A) zeolite, which is available commercially. Such naturally occurring zeolites include the following materials, set forth by way of illustration and not for purposes of limitation: Brewsterite, Edingtonite, Epistilbite, Gismondine, Laumontite, Mesolite, Phillipsite, Scolecite, and Stilbite.

The most preferred zeolite molecular seive of choice for use in this invention, as noted, is the synthetic 3A (i.e., potassium-exchanged zeolite A) zeolite such as produced by the Linde Division of Union Carbide Corporation. The type 3A Linde zeolite has a pore size of about 3 Angstroms, and a typical non-limiting example of a commercial embodiment of this material has the following characteristics: a particle size (pelletized) of 1/16", a bulk density of 40 lb./cu ft., a water content of 1.5 weight %, and a water capacity of 20 weight %. It is to be understood, of course, that a number of other commercially acceptable forms of type 3A zeolite of different description are available and acceptable for use in the present invention, and this would be apparent to those skilled in the art.

While the preferred embodiment of this invention (and substantially all the preceding discussion concerning said invention) has been described in terms of ethanol and its dehydration, in view of the great commercial importance of anhydrous ethanol (particularly as a raw material for manufacture of gasohol) and the unique suitability the present dehydration process has with respect to ethanol, nevertheless it is to be noted that the present dehydration process can profitably be employed in the production of other anhydrous alcohols as well. In general, the present dehydration process can be applied to dehydrate alcohols that form azeotropes with water, preferably $C_2$-$C_5$ alkanols such as ethanol, n-propanol, isopropanol, n-butanol, secondary butanol, tertiary butanol, and secondary amyl alcohol. However, in order to provide beneficial results, it is necessary that, upon distillation of the crude $C_2$-$C_5$ alcoholic feedstock at elevated pressure, a vapor be obtained and removed at a concentration less than that of the azeotrope of the alcohol contained in said feedstock, consistent with the economics of the process, it being understood that, the farther removed from azeotropic formation, the greater the need for additional circulation of the inert gas used, a factor well within the skill of the art to work out for itself. The resultant gaseous overhead admixture from the distillation can then be dried in the presence of the inert gas, i.e., $CO_2$ or $N_2$, which cannot be adsorbed by the type 3A zeolite adsorbent, and the drying process employed is as previously described above for the drying of ethanol. It would be well within the skill of those skilled in the art to develop operable process parameters (e.g., temperatures and pressures) for each alcoholic feedstock for which dehydration thereof was desired in view of the teachings of the present invention.

Wherever used herein, the term % is understood to be in terms of weight %, unless otherwise specified in terms of mole %.

It is to be understood that the expression "condensing the dried alcoholic (e.g., ethanolic) product at an ambient temperature", whenever used herein, has reference to the capability of the present dehydration process to allow such condensation to take place without need of any additional thermal energy beyond the energy supplied to the first stage distillation column such as, for example, a new or independent source of energy commensurate with the energy needs required to condense the dried alcoholic (e.g., ethanolic product) at an ambient temperature.

It is to be further understood that the term "purging" is meant to refer to the use of the inert gas (i.e., $CO_2$ or $N_2$) employed to sweep vapors, intended for removal, from the site of removal, whereas the term "repressurization" is intended to connote the use of the inert gas of the same identity to elevate the pressure, to the level desired, of the adsorption vessel into which it is introduced.

Concerning the form of nitrogen employed as an inert gas, the preferred source comprises the usual standard commercial forms. The use of air, however, as a source of nitrogen would not be desirable in view of the hazards that would arise with such use through the formation of air-alcohol admixtures that could, under conditions of the present invention, be combustible.

With reference to the adsorption cycles utilized with respect to the drying of ethanol, their duration can vary from one half minute to ten minutes in length, preferably three minutes in length. As depicted in FIG. 4, moreover, it will be understood that such adsorption cycles, illustrated in terms of consecutive, precise three-minute terms, are illustrated in theoretical terms; in practice, however, some minimal time would be lost in order to accommodate opening and closing of the valves required to effect the starting and stopping points of individual adsorption cycles.

Finally, as noted previously with reference to the first stage distillation, it is necessary that this be conducted to a desired point short of formation of the azeotrope of the feed alcohol, so that a gaseous overhead can be removed, at a concentration less than that of the azeotrope of said alcohol. For ethanol, this point economically speaking, is arrived at when the overhead from the distillation stage contains about 78 mole % (about 90 weight %) ethanol. For other alcohols, this point might involve a different concentration of alcohol, consistent with the process economics involved. As previously noted, there is a "trade-off" possible between the amount of circulating inert gas used and the alcohol concentration of the distillate desired short of azeotropic formation, whereby more inert gas has to be circulated, essentially for cooling purposes, to compensate for the extent one wishes to move from the threshhold of azeotropic formation.

While the invention has been described in connection with an exemplary embodiment thereof, it will be understood that many modifications will be apparent to those of ordinary skill in the art and that this application is intended to cover such modifications or any adaptations or variations thereof.

What I claim is:

1. A process for the dehydration of ethanol comprising distilling, at an elevated pressure, a crude aqueous ethanol feedstock to produce a gaseous ethanol-$H_2O$ mixture comprising at least about 75 mole % ethanol; admixing an amount of $CO_2$ with said mixture to form an admixture; drying said gaseous admixture with an adsorbent consisting essentially of a type 3A crystalline zeolite; and condensing the dried ethanolic product at an ambient temperature; said elevated pressure and said amount being sufficient to permit condensation of said product at ambient temperatures.

2. A process according to claim 1, wherein said feedstock is a fermentation ethanolic product.

3. A process according to claim 2, wherein the gaseous $CO_2$ is derived from a fermentation ethanol process.

4. A process according to claim 1, wherein said elevated pressure is a pressure of at least 50 p.s.i.a.

5. A process according to claim 1, wherein said mixture comprises about 78 mole % ethanol.

6. A process according to claim 1, wherein the temperature of said admixture is maintained above the dewpoint of the ethanol in said admixture prior to said admixture being dried.

7. A process according to claim 1, wherein said drying is alternately effected in a series of at least two closed vessels having an inlet and an outlet and the adsorbent contained therein, the sensible heat of adsorption generated during drying being substantially confined to intermediate levels in said adsorbent for regenerating said adsorbent.

8. A process according to claim 7, wherein drying of said gaseous admixture is effected in one of said vessels concurrently while the regeneration of the adsorbent in the other of said vessels is being effected.

9. A process according to claim 7, wherein said drying is periodically effected in a series of three closed vessels having an inlet and an outlet and the adsorbent contained therein, whereby drying of said adsorbent is effected in one of said vessels while regeneration of the adsorbent in another of said vessels and purging of the adsorbent in the third of said vessels are being effected.

10. A process according to claim 7, wherein said drying is periodically effected in a series of three closed vessels having an inlet and an outlet and the adsorbent contained therein, whereby drying of said adsorbent is effected in one of said vessels while regeneration of the adsorbent in another of said vessels and repressurization of the adsorbent in the third of said vessels are being effected.

11. A process according to claim 11, wherein the temperature of said distilled admixture is maintained above the dewpoint of the ethanol in said admixture prior to said admixture being dried.

12. A process according to claim 11, wherein said drying is alternately effected in a series of at least two closed vessels having an inlet and an outlet and the adsorbent contained therein, the sensible heat of adsorption generated during drying being substantially confined to intermediate levels in said adsorbent in regenerating said adsorbent.

13. A process according to claim 11, wherein drying of said gaseous admixture is effected in one of said vessels concurrently while regeneration of the adsorbent in the other of said vessels is being effected.

14. A process according to claim 11, wherein said drying is periodically effected in a series of three closed vessels having an inlet and an outlet and the adsorbent contained therein, whereby drying of said adsorbent is effected in one of said vessels while regeneration of the adsorbent in another of said vessels and purging of the adsorbent in the third of said vessels are being effected.

15. A process according to claim 11, wherein said drying is periodically effected in a series of three closed vessels having an inlet and an outlet and the adsorbet contained therein, whereby drying of said adsorbent is effected in one of said vessels while regeneration of the adsorbent in another of said vessels and repressurization of the adsorbent in the third of said vessels are being effected.

16. A process for the dehydration of ethanol comprising distilling, at a pressure of at least about 50 p.s.i.a., a crude fermentation aqueous ethanol product to produce a gaseous ethanol-$H_2O$ admixture containing about 78 mole % ethanol; diluting said admixture with an amount of gaseous $CO_2$; drying said diluted gaseous admixture with a type 3A crystalline zeolite; said pressure and said amount being sufficient to permit condensation of a dried ethanolic product at ambient temperatures; and condensing the dried ethanolic product at an ambient temperature.

17. A process for the dehydration of a $C_2$—$C_5$ alkanol comprising distilling, at an elevated pressure, a crude aqueous feedstock comprising said alkanol to an extent short of formation of the azeotrope of said alkanol; adding an amount of an inert gas selected from the group consisting of $CO_2$ and $N_2$ to form an admixture; drying the resultant gaseous admixture with an absorbent consisting essentially of a type 3A crystalline zeolite; said pressure and said amount being sufficient to permit condensation of a dried alkanol product at ambient temperatures; and condensing the dried alkanol product at an ambient temperature.

18. A process according to claim 17, wherein said drying is alternately effected in a series of at least two closed vessels having an inlet and an outlet and the adsorbent contained therein, the sensible heat of adsorption generated during drying being substantially confined to intermediate levels in said adsorbent for regenerating said adsorbent.

19. A process according to claim 17, wherein drying of said gaseous admixture is effected in one of said vessels concurrently while the regeneration of the adsorbent in the other of said vessels is being effected.

20. A process according to claim 17, wherein said drying is periodically effected in a series of three closed vessels having an inlet and an outlet and the adsorbent contained therein, whereby drying of said adsorbent is effected in one of said vessels while regeneration of the adsorbent in another of said vessels and purging of the adsorbent in the third of said vessels are being effected.

21. A process according to claim 17, wherein said drying is periodically effected in a series of three closed vessels having an inlet and an outlet and the adsorbent contained therein, whereby drying of said adsorbent is effected in one of said vessels while regeneration of the adsorbent in another of said vessels and repressurization of the adsorbent in the third of said vessels are being effected.

22. A process for the production of an ethanol-gasoline fuel for internal combustion engines, comprising distilling, at an elevated pressure, a crude aqueous ethanol feedstock to produce a gaseous ethanol-$H_2O$ mixture comprising at least about 75 mole % ethanol; adding an amount of an inert gas selected from the group consisting of $CO_2$ and $N_2$; drying said gaseous admixture with an adsorbent consisting essentially of a type 3A crystalline zeolite; said pressure and said amount being sufficient to permit condensation of a dried ethanolic product at ambient temperatures; condensing the dried ethanolic product at an ambient temperature; recovering the anhydrous ethanol; and mixing said anhydrous ethanol with sufficient gasoline so as to produce an ethanol-gasoline blend suitable for use as said fuel.

23. A process for the production of an ethanol-gasoline fuel for internal combustion engines, comprisng distilling, at a pressure of at least about 50 p.s.i.a., a crude fermentation aqueous ethanol product to produce a gaseous ethanol-$H_2O$ admixture containing about 78 mole % ethanol; diluting said admixture with an amount of gaseous $CO_2$; drying said diluted gaseous admixture with a type 3A crystalline zeolite; said pressure and said amount being sufficient to permit condensation of a dried ethanolic product at ambient temperatures; condensing the dried ethanolic product at an ambient temperature; recovering the anhydrous ethanol product; and mixing said anhydrous ethanol with sufficient gasoline so as to produce an ethanol-gasoline blend suitable for use as said fuel.

* * * * *

UNITED STATES PATENT AND TRADEMARK OFFICE
CERTIFICATE OF CORRECTION

PATENT NO. : 4,273,621

DATED : June 16, 1981

INVENTOR(S) : Louis L. Fornoff

It is certified that error appears in the above-identified patent and that said Letters Patent are hereby corrected as shown below:

Column 12, line 67, the number "11" (first occurrence) should read -- 12 --;

Column 13, line 3, the number "12" should read -- 13 --;

line 10, the number "13" should read -- 14 --;

line 14, the number "14" should read -- 15 --;

line 21, the number "15" should read -- 16 --; and line 29, the number "16" should read -- 11 --.

Signed and Sealed this

Twenty-ninth Day of September 1981

[SEAL]

Attest:

GERALD J. MOSSINGHOFF

Attesting Officer

Commissioner of Patents and Trademarks